United States Patent [19]
Frommer et al.

[11] 3,937,817
[45] Feb. 10, 1976

[54] PHARMACEUTICAL COMPOSITIONS CONTAINING A SACCHARASE INHIBITOR
[75] Inventors: Werner Frommer; Walter Puls; Delf Schmidt, all of Wuppertal, Germany
[73] Assignee: Bayer Aktiengesellschaft, Leverkusen, Germany
[22] Filed: June 20, 1974
[21] Appl. No.: 481,224

Related U.S. Application Data
[62] Division of Ser. No. 336,741, Feb. 28, 1973.

[52] U.S. Cl................. 424/115; 195/80 R; 424/181
[51] Int. Cl.²........................................ A61K 35/00
[58] Field of Search.................... 424/115; 195/80 R

[56] References Cited
UNITED STATES PATENTS

| | | | |
|---|---|---|---|
| 3,629,404 | 12/1971 | Florent et al. ................. | 195/80 R X |
| 3,806,421 | 4/1974 | Veda et al. ..................... | 424/115 X |
| 3,855,066 | 12/1974 | Frommer et al. ................ | 424/115 X |

*Primary Examiner*—Leonard Schenkman
*Attorney, Agent, or Firm*—Depaoli & O'Brien

[57] ABSTRACT

The invention relates to a saccharase inhibitor derived from Actinoplanaceae Strain CBS 961.70, including mutants and variants thereof, means for the production of said saccharase inhibitors comprising cultivation of Actinoplanaceae Strain CBS 961.70, including mutants and variants thereof, in appropriate nutrient solutions which are characterized by being starch free under conditions most favorable to growth and production of said saccharase inhibitor and recovering a saccharase inhibitor from culture broths of said nutrient solutions, as well as the use of said inhibitor in pharmaceutically acceptable therapeutic compositions suitable for use in the treatment and relief of conditions indicative of adiposity, diabetes, pre-diabetes, hyperlipaemia (atherosclerosis), caries and the like.

2 Claims, No Drawings

PHARMACEUTICAL COMPOSITIONS CONTAINING A SACCHARASE INHIBITOR

This is a division, of copending application Ser. No. 336,741 filed Feb. 28, 1973.

BACKGROUND OF THE INVENTION

It is known that in animals and man, after consumption of foodstuffs and beverages containing saccharose, hyperglycaemias occur which are caused by rapid splitting of the saccharose by saccharases of the digestive tract according to the following equation

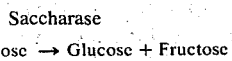

Saccharose → Glucose + Fructose

These hyperglycaemias are particularly strong, and of long-lasting pronounced character, with diabetics. With adipose subjects, the alimentary hyperglycaemia frequently causes a particularly intense insulin secretion which in turn leads to increased fat synthesis and reduced fat degradation.

These saccharase inhibitors according to the invention, obtained and isolated according to the above methods, considerably reduce the alimentary hyperglycaemia and hyperinsulinaemia in rats dosed with saccharose.

It is furthermore known that caries occur particularly strongly and frequently after consumption of beverages and foodstuffs containing saccharose [for example, B. W. Gold: Advances in Applied Microbiology 11 (1969) 135-157]. An inhibition of the splitting of saccharose by the inhibitors according to the invention reduces the formation of cariogenic substances.

These inhibitors are therefore suitable for use as a therapeutic agent for the following indications: adiposity, hyperlipaemia (atherosclerosis), diabetes, prediabetes and caries.

RELATIONSHIP TO COPENDING APPLICATIONS

United States patent application Ser. No. 213,066, filed Dec. 28, 1971, now U.S. Pat. No. 3,876,766, entitled "GLYCOSIDE-HYDROLASE ENZYME INHIBITORS" discloses that microorganisms of the order Actinomycetales form inhibitors for glycoside-hydrolases, and in particular inhibitors for glycoside-hydrolases of preferentially carbohydrate-splitting enzymes of the digestive tract. One group of these inhibitors is relatively heat-stable and stable to acid and alkali at room temperature. Chemically speaking, these inhibitors belong to the class of the oligosaccharides or polysaccharides or their derivatives.

Thus, for example, in Examples 28–38 of the aforesaid application describes the isolation of such an amylase inhibitor derived from the Actinoplanaceae strain CBS 961.70 belonging to the order Actinomycetales. The culture solutions resulting from fermentations of this strain under optional conditions contain about 30,000-40,000 AIU/ml., and the purest inhibitors isolated therefrom possess specific activities of 3-8 × 10⁶ amylase inhibitor units (AIU $\mu$g).

In copending application Ser. No. 336,687, filed Feb. 28, 1973, now U.S. Pat. No. 3,855,066, there is disclosed the production of amylase inhibitors from strain CBS 614.71 by cultivating the same in a nutrient medium containing starch.

THE PRESENT INVENTION

It has now been discovered that by the use of the Actinoplanaceae strain CBS 961.70, including the new strain CBS 614.71 and its mutants and variants, in conjunction with nutrient solutions which are free from starch cultures containing more than 10 SIU/ml can be obtained.

The invention, accordingly, provides a novel process for the production of a saccharase inhibitor which comprises culturing a microorganism of the family Actinoplanaceae, Strain CBS 961.70, a mutant or variant thereof, in a nutrient culture which does not contain starch under aerobic conditions for a period of time sufficient for the production of said saccharase inhibitor and separating said saccharase inhibitor from said nutrient culture medium.

As used herein, the expression "a mutant or variant" of Strain CBS 961.70 is defined as strains derived from Strain CBS 961.70 by mutations either spontaneous or induced such as by bombardment with mutagenic radiation and variants of the strain produced from it by processes other than mutations. Strain CBS 614.71 is an example of such a mutant or variant.

In the specification and claims the abbreviation "CBS" refers to strains that have been deposited at the Centraalbureau voor Schimmelcultures, Baarn, Netherlands, under the stated Accession Number.

It has been found that the culture solutions of the Strain CBS 961.70 prepared in accordance with the techniques of copending application Ser. No. 213,066, filed Dec. 28, 1971, now U.S. Pat. No. 3,876,766 frequently also possess a slight saccharase-inhibiting activity, but the isolation and preparation in pure form of the saccharase inhibitor formed is very difficult due to the presence of considerable amounts of amylase inhibitor in the culture solution.

It has now been discovered that it is possible to suppress the formation of amylase inhibitor while at the same time promoting the formation of saccharase inhibitor.

This invention provides a method of producing a saccharase inhibitor comprising growing Actinoplanaceae Strain CBS 961.70 or a mutant or variant thereof in a starch-free nutrient medium to produce a culture, and separating the saccharase inhibitor from the culture.

In this method, the nutrient medium must be free of starch. A preferred nutrient medium is a solution having the composition 3.5 percent of glucose, 0.5 percent of casein hydrolysate, 1.3 percent of yeast extract, 0.3 percent of $K_2HPO_4$ and 0.3 percent of $CaCO_3$; pH adjusted to 7.8 with KOH before sterilization. Such solutions after innoculation and several days' fermentation with Strain CBS 961.70, yield cultures which contain more than 10 SIU/ml (SIU = Saccharase Inhibitor Unit). At a content of 300 – 700 AIU/ml (AIU = Amylase Inhibitor Unit) an SIU/AIU ratio of $15 \times 10^{-3} - 30 \times 10^{-3}$ results. (f = SIU/AIU × 10³).

The yield of saccharase inhibitor in the method of the invention can be increased further if maltose is added to the nutrient solution. If, for example, 1.5 percent of maltose is added to the above-mentioned nutrient solution, culture broths containing 16 – 18, and even up to 24, SIU/ml are obtained.

A decisive factor in obtaining a favorable SIU/AIU ratio is the duration of growth. If growth is stopped shortly before reaching, or just on reaching, the maximum SIU content, which depending on the inoculation can happen after only 1.5 to 2 days' fermentation, f-values of up to 180 are obtained.

As has heretofore been stated, instead of the Strain CBS 961.70 it is also possible to use its mutants and variants such as Strain CBS 614.71.

The saccharase inhibitor can be isolated from the appropriately fermented culture solution by any suitable method. One such method is concentrating the culture broth in vacuo to 1/10 – 1/20 of the original volume, with subsequent lyophilization. Alternatively the inhibitor may be precipitated from the concentrated broth with 4 – 10 parts by volume of organic solvent such as an alcohol or ketone, preferably with 5 – 9 parts by volume of acetone. One preferred and particularly simple method is adsorption of the inhibitor from the neutral (preferably pH 5–8) culture solution on 0.5 – 4 percent, preferably 1–2 percent of active charcoal and subsequent desorption with an aqueous alcohol or aqueous acetone, especially at acid pH values, preferably with 50 percent strength aqueous acetone at pH 2–3. The desorbate is subsequently concentrated in vacuo to 1/50 – 1/200, preferably 1/100, of the initial volume (of the culture) and is subsequently precipitated with organic solvents, preferably acetone. In general, in order to isolate purer preparations, a preliminary adsorption of the brown dyestuffs which contaminate the culture solution is preferably carried out on 1 – 2 percent of active charcoal at acid pH values (pH values of 1–4, preferably 2–3), at which low pH, surprisingly, the adsorption of the saccharase inhibitor does not occur to a significant extent.

The present invention also includes a pharmaceutical composition containing as an active ingredient the saccharase inhibitor produced by the method of this invention, in admixture with a solid or semi-liquid diluent.

Examples of such diluents include: (a) fillers and extenders, e.g., starch, sugars, mannitol, and silicic acid; (b) binding agents, e.g., carboxymethyl cullulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The inhibitor may also be added to foodstuffs and beverages containing saccharose.

Particular examples of the pharmaceutical compositions of this invention are suspensions, granules, chewing gum, toothpaste, foodstuffs and beverages containing the saccharase inhibitor.

The saccharase inhibitor produced by the method of this invention is generally to be administered orally in amounts of 100–10,000 SIU/kg body weight per therapeutic administration, which will be once or several times daily before, during or after meals.

The invention further provides medicaments in dosage unit form containing saccharase inhibitor produced by the method of the invention.

The term "medicament in dosage unit form" as used here means physically discrete coherent portions suitable for medical administration, each containing a predetermined individual quantity of the inhibitor, the said quantity being such that one portion is required for a single therapeutic administration in accordance with guidelines set forth above. Examples of such medicaments in dosage unit form according to the invention are tablets, dragees, capsules, sticks of chewing gum and ampoules containing the inhibitor.

AMYLASE TEST

One amylase inhibitor unit (1 AIU) is defined as the amount of inhibitor which inhibits two amylase units to the extent of 50 percent. One amylase unit (AU) is the amount of enzyme which in one minute, under the test conditions indicated below, splits 1 $\mu$ equivalent of glucosidic bonds in starch. The $\mu$ equivalent of split bonds are determined colorimetrically with dinitrosalicyclic acid as $\mu$ equivalent of reducing sugar formed and are quoted, with the aid of a maltose calibration curve, as $\mu$ equivalent of maltose equivalents. To carry out the test, 0.1 ml of amylase solution (20 – 22 AU/ml) is mixed with 0 – 10 $\mu$g of inhibitor or 0–20 $\mu$g of the solution to be tested in 0.4 ml of 0.02 M sodium glycerophosphate buffer/0.001 M $CaCl_2$ at pH 6.9 and equilibrated for about 10 – 20 minutes in a water bath at 35°C. The mixture is then incubated for 5 minutes at 35°C with 0.5 ml of a 1 percent strength starch solution (soluble starch of Messrs. Merck, Darmstadt, No. 1252) which has been prewarmed to 35°C, and 1 ml of dinitrosalicylic acid reagent (according to P. Bernfeld in Colowick-Kaplan, Meth. Enzymol., Volume 1, page 149) is then added. To develop the color, the batch is heated for 5 minutes on a boiling water bath, then cooled and treated with 10 ml of distilled water. The extinction at 540 nm is measured against a correspondingly made-up blank without amylase. For evaluation, the amylase activity which is still present after addition of inhibitor is read off from a previously recorded amylase calibration curve and the percentage inhibition of the amylase employed is calculated therefrom. The percentage inhibition is plotted as a function of the quotient $$\frac{\mu g \text{ inhibitor}^*}{AU^{**}}$$

*relative to dry substance
**AU in the non-inhibited batch of the same series and the 50% inhibition point is read off from the curve and converted to AIU/mg of inhibitor.

SACCHARASE TEST

One saccharase inhibitor unit (SIU) is defined as the amount of inhibitor which inhibits two saccharase units to the extent of 50 percent. One saccharase unit (SU) is the amount of enzyme which in 1 minute, under the test conditions indicated below, splits 1 $\mu$mol of saccharose into glucose and fructose. The $\mu$mol of glucose formed is determined quantitatively with the aid of the glucose oxidase reaction under conditions under which further splitting of saccharose by the saccharase no longer occurs. To carry out the test, 0.05 ml of a saccharase solution[1]) adjusted to 0.12 SU is mixed with 0 – 20 $\mu$g of inhibitor or 0–20 $\mu$l of the solution to be tested and made up to 0.1 ml with 0.1 M sodium maleate buffer of pH 6.0. The mixture is equilibrated for 10 minutes at 35°C and then mixed with 0.1 ml of an 0.05 M saccharose solution in 0.1 M sodium maleate buffer of pH 6.0, which has been prewarmed to 35°C. The mixture is incubated for 20 minutes at 35°C and the saccharase reaction is stopped by adding 1 ml of glucose oxidase reagent[2]) and incubated for a further 30 minutes at 35°C. Thereafter, 1 ml of 50 percent strength $H_2SO_4$ is added and the mixture is measured at 545 nm against a corresponding blank. For evaluation, the percentage inhibition of the saccharase employed is calculated and converted, from the 50 percent inhibition point, with the aid of a glucose calibration curve, to SIU/g or SIU/liter.

[1]. Solubilized saccharase from the mucous membrane of the small intestine of pigs, according to B. Borgstrom and A. Dahlquist, Acta Chem. Scand. 12, (1958), page 1997. Diluted with 0.1 M sodium maleate buffer of pH 6 to the appropriate SU content.

[2]. The glucose oxidase reagent is made by dissolving 2 mg of glucose oxidase (Messrs. Boehringer No. 15,423 EGAB) in 100 ml of 0.565 M tris-HCl-buffer of pH 7 and subsequently adding 1 ml of detergent solution (2 g of Triton 100 + 8 g of 95 percent strength ethanol, analytical grade), 1 ml of dianisidine solution (260 mg of o-dianisidine 0.2HCl in 20 ml of $H_2O$) and 0.5 ml of 0.1 percent strength aqueous peroxidase solution (Messrs. Boehringer No. 15,302 EPAP).

The following examples illustrate the best mode now contemplated for carrying out the invention.

EXAMPLE 1

1 liter Erlenmeyer flasks containing 120 ml of a nutrient solution of composition 3.5 percent of glucose, 0.5 percent of casein hydrolysate, 1.3 percent of yeast extract, 0.3 percent of $CaCO_3$, 0.3 percent of $K_2HPO_4$, (the pH being adjusted prior to sterilization to 7.8 with KOH and the solution being sterilized for 30 minutes at 121°C), are inoculated with 4 ml of a 3-day old pre-culture of Strain CBS 961.70 in a nutrient solution of composition 3 percent of glycerine, 3 percent of soya flour and 0.2 percent of $CaCO_3$, obtained by incubation on a rotary shaking machine at 28°C, and the charges are incubated at 24°C after 3 days of incubation, a culture broth is obtained which contains 9.1 SIU/ml and 240 AIU/ml and after 4 days' incubation contains 10.4 SIU/ml and 675 AIU/ml.

EXAMPLE 2

When maltose in various concentrations is added to the nutrient solution used in Example 1 and the solution is inoculated and incubated according to Example 1, the following yields of SIU/ml and AIU/ml are obtained:

| Maltose concentration % | After 3 days | | After 5 days | |
|---|---|---|---|---|
| | AIU/ml | SIU/ml | AIU/ml | SIU/ml |
| 0 | 363 | 11.2 | 444 | 8.8 |
| 0.5 | 479 | 12.7 | 614 | 11.3 |
| 1.0 | 383 | 13.6 | 688 | 12.5 |
| 1.3 | 337 | 15.7 | 725 | 12.7 |
| 1.8 | 274 | 16.6 | 678 | 14.4 |
| 2.2 | 287 | 16.8 | 600 | 15.5 |

EXAMPLE 3

To the nutrient solution of Example 1 is added 1.3 percent of maltose and the procedure of Example 1 is repeated, a culture broth is obtained which after 2 days' fermentation contains 14.4 SIU/ml and 81 AIU/ml and after 4 days' fermentation contains 14.5 SIU/ml and 580 AIU/ml.

EXAMPLE 4

1 liter Erlenmeyer flasks which contain 120 ml of a nutrient solution of composition 3 percent of glucose, 1 percent of maltose, 0.5 percent of casein hydrolysate, 1.3 percent of yeast extract, 0.3 percent of $CaCO_3$, 0.3 percent of $K_2HPO_4$ (the pH being adjusted to 7.2 with $Na_2CO_3$ before sterilization and the mixture being sterilized for 30 minutes at 121°C) are inoculated with 4 ml of a 3 days' old pre-culture of Strain CBS 961.70 in a nutrient solution of composition 3 percent of glycerine, 3 percent of soya flour, 0.2 percent of $CaCO_3$, obtained by incubation on a rotary shaking machine at up to 28°C, and the batch is incubated at 24°C after 4 days of incubation, a culture broth is obtained which contains 22 SIU/ml and 500 AIU/ml.

EXAMPLE 5

500 ml of a brown culture solution of the Strain CBS 961.70 fermented according to Example 4 and containing 22,000 SIU/liter were adjusted to pH 2.5 with half-concentrated $HNO_3$, treated with 5 g of active charcoal (Messrs. Merck) and stirred for 10 minutes. The mixture was centrifuged for 15 minutes at 10,000 rpm and the clear, yellow supernatant liquid was neutralized with ammonia. Thereafter it was concentrated to 50 ml on a rotary evaporator at 20 mm Hg and this concentrated solution was treated with 50 ml of acetone to precipitate inactive constituents. The clear filtrate was added dropwise to 400 ml of acetone while stirring and the precipitate which formed was collected on a filter, washed with acetone and ether and dried in vacuo at room temperature. Yield: 1.4 g with 6,000 SIU/g ≙ 70 percent yield, relative to the activity.

EXAMPLE 6

500 ml of a culture solution of the Strain CBS 961.70 fermented according to Example 4 and containing 22,000 SIU/liter were worked up according to Example 5 but were precipitated with ethanol instead of with acetone. Yield: 0.6 g with 7,000 SIU/g ≙ 38 percent yield, relative to the activity.

EXAMPLE 7

1 liter of a dark brown culture solution (21,000 SIU/liter) fermented analogously to Example 4 was adjusted to pH 2.5 with half-concentrated nitric acid, 10 g of active charcoal (Messrs Merck) and 10 g of the filter aid Clarcell were added and the mixture was stirred for 10 minutes. It was filtered through a filter provided with a 1 – 2 cm high Clarcell layer and the filtrate was neutralized with ammonia. The filter cake was discarded. 1.5 percent of active charcoal were added to the neutral filtrate (19,000 SIU/liter) and the mixture was stirred for 10 minutes and then again filtered. The filtrate still contained approximately 10 percent of the activity and was discarded. (If this residual activity is also to be isolated, a further adsorption with 0.5 percent of active charcoal is carried out and the charcoal residues are combined). The charcoal residue containing the saccharase activity was washed with a little water and then stirred 3 times for 10 minutes with 50 ml portions of 50 percent strength acetone at pH 2.5 (HCl) for desorption of the activity. Thereafter, the mixture was in each case filtered and the three desorbates were combined. They were concentrated to 10 ml in a rotary evaporator and the viscous concentrate was treated with the same volume (10 ml) of methanol, while stirring. The precipitate formed was centrifuged off. The clear light brown 50 percent strength solution in methanol was then added dropwise, while stirring, to 250 ml (= 12.5 volumes) of absolute acetone. The precipitate formed settled out well and after decanting the deep yellow supernatant liquid the residue was taken up in absolute acetone and washed. It was filtered off and further rinsed once with absolute acetone and once with ether. Thereafter it was dried in vacuo at room temperature. Yield: 850 mg with 12,500 SIU/g the retro-orbital venous plexus. Blood glucose is determined in an autoanalyzer [Technicon according to Hoffman: J. biol. Chem. 120, 51 (1937)], and serum insulin according to the methods of Hales and Randle: Biochem. J. 88, 137 (1963).

TABLE 1

Average blood glucose values in mg/100 ml ± ls of fasting rats at various times after oral administration of saccharose ± active compound analogously to Example 5.

| Dose/kg, administered orally | 10 | 20 | 30 | 60 | 120 min. |
|---|---|---|---|---|---|
| Control without saccharose | 67 ± 7.1 | 72 ± 4.6 | 68 ± 5.3 | 66 ± 5.0 | 71 ± 3.3 |
| Control with saccharose | 134 ± 15 | 140 ± 16 | 126 ± 12 | 117 ± 20 | 103± 3.0 |
| 100 SIU in saccharose | 96 ± 4.4 | 93 ± 6.2 | 92 ± 5.6 | 92 ± 3.4 | 95 ± 11 |

Legend
$P < 0.05$
$P < 0.001$ against control with saccharose

TABLE 2

Average serum insulin values in $\mu$U/ml ± ls of fasting rats at various times after oral administration of saccharose ± active compound analogously to Example 5.

| Dose/kg, administered orally | 10 | 20 | 30 | 60 | 120 min. |
|---|---|---|---|---|---|
| Control without saccharose | 8.8 ± 1.8 | 9.8 ± 1.4 | 10.8 ± 2.3 | 10.7 ± 4.6 | 8.1 ± 0.7 |
| Control with saccharose | 22.2 ± 11 | 35.3 ± 14 | 19.3 ± 5.0 | 16.7 ± 5.3 | 8.1 ± 1.1 |
| 100 SIU in saccharose | 9.9 ± 4.3 | 11.1 ± 3.5 | 7.6 ± 1.7 | 14.8 ± 3.8 | 10.2 ± 2.8 |

Legend
$P < 0.05$
$P < 0.01$
$P < 0.001$ against control with saccharose

≙ 51 percent yield (relative to units in the culture broth).

TABLE (Activity yields from working up)

| | Working-up Step | Volume (ml) | SIU/L | AIU/L | $f = \frac{SIU}{AIU} \times 10^3$ | SIU | SIU Yield (%) |
|---|---|---|---|---|---|---|---|
| 1) | Original solution | 1,000 | 21,000 | $0.5 \times 10^6$ | 42 | 21,000 | 100 |
| 2) | After 1st active charcoal adsorption (pH 2.5) | 1,000 | 19,000 | $0.4 \times 10^6$ | 48 | 19,000 | 90 |
| 3) | After 2nd active charcoal adsorption (pH 7.0) | 1,000 | 2,000 | | | 2,000 | (discarded: 10%) |
| 4) | 1st desorbate | 45 | 260,000 | $3.5 \times 10^6$ | 75 | 11,500 | 55 ⎫ |
| 5) | 2nd desorbate | 45 | 92,000 | $2 \times 10^6$ | 46 | 4,100 | 19.5 ⎬ 81 |
| 6) | 3rd desorbate | 45 | 30,000 | $0.75 \times 10^6$ | 40 | 1,350 | 6.5 ⎭ |
| 7) | Concentrated to 10 ml on rotary evaporator | 10 | 1,500,000 | $22 \times 10^6$ | 68 | 15,000 | 72 |
| 8) | 50% methanol precipitation (filtered) | 18 | 730,000 | $12 \times 10^6$ | 61 | 13,200 | 63 |
| 9) | Supernatant liquid from acetone precipitation | 260 | 8,400 | | | 2,200 | (discarded: 10%) |
| 10) | Precipitate | 0.85 g | 12,500 /g | $0.22 \times 10^6$ /g | 56 | 10,600 | 51 |

EXAMPLE 8

(Experimental arrangements for demonstrating the action of saccharase inhibitors on rats)

To produce an alimentary hyperglycaemia and hyperinsulinaemia fasting rats (n = 6) are given 2.5 g/kg of saccharose orally. Six other rats are given, additionally to the saccharose, the saccharase inhibitor manufactured analogously to Example 5, in the indicated dosage. The blood glucose and the serum insulin are examined at the indicated time intervals after administration of saccharose. The blood samples are obtained from

What is claimed is:

1. A pharmaceutical composition containing as an active ingredient a therapeutically effective quantity of a saccharase inhibitor mixed with a solid or semi-liquid diluent, wherein said saccharase inhibitor is produced by a method comprising growing Actinoplanaceae strain CBS 961.70 in a starch-free nutrient medium to produce a culture and separating the saccharase inhibitor from the culture.

2. A pharmaceutical composition containing as an active ingredient a therapeutically effective quantity of a saccharase inhibitor mixed with a solid or semi-liquid diluent, wherein said saccharase inhibitor is produced by a method comprising growing Actinoplanaceae strain CBS 614.71 in a starch-free nutrient medium to produce a culture and separating the saccharase inhibitor from the culture.

* * * * *

UNITED STATES PATENT OFFICE
CERTIFICATE OF CORRECTION

Patent No. 3,937,817　　　　　　　　　Dated February 10, 1976

Inventor(s) Werner Frommer et al

It is certified that error appears in the above-identified patent and that said Letters Patent are hereby corrected as shown below:

Table 1, under 120 minutes "95 $\pm$ 11" should be --95 $\pm$ 12--.

Signed and Sealed this

Third Day of August 1976

[SEAL]

Attest:

RUTH C. MASON　　　　　　　　　　　C. MARSHALL DANN
Attesting Officer　　　　　　　　　Commissioner of Patents and Trademarks